(12) United States Patent
Evison

(10) Patent No.: US 9,034,306 B2
(45) Date of Patent: May 19, 2015

(54) DEPILATORY COMPOSITION COMPRISING HYDROPHOBIC PARTICLES, PROCESS FOR PREPARATION AND METHOD OF USE

(75) Inventor: Jane Evison, Hull (GB)

(73) Assignee: RECKITT & COLMAN (OVERSEAS) LIMITED, Slough, Berkshire (GB)

( * ) Notice: Subject to any disclaimer, the term of this patent is extended or adjusted under 35 U.S.C. 154(b) by 640 days.

(21) Appl. No.: 12/812,722

(22) PCT Filed: Dec. 24, 2008

(86) PCT No.: PCT/GB2008/004288
§ 371 (c)(1),
(2), (4) Date: Sep. 28, 2010

(87) PCT Pub. No.: WO2009/090362
PCT Pub. Date: Jul. 23, 2009

(65) Prior Publication Data
US 2011/0166583 A1    Jul. 7, 2011

(30) Foreign Application Priority Data

Jan. 14, 2008 (GB) .................................. 0800570.4

(51) Int. Cl.
| | |
|---|---|
| *A61Q 9/04* | (2006.01) |
| *A61K 8/81* | (2006.01) |
| *A61K 8/73* | (2006.01) |

(52) U.S. Cl.
CPC .............. *A61K 8/8182* (2013.01); *A61K 8/732* (2013.01); *A61Q 9/04* (2013.01)

(58) Field of Classification Search
CPC ........ A61K 8/732; A61K 8/8182; A61Q 9/04
See application file for complete search history.

(56) References Cited

U.S. PATENT DOCUMENTS

| | | | | |
|---|---|---|---|---|
| 6,096,345 | A | * | 8/2000 | Narayanan et al. ............ 424/501 |
| 2003/0044374 | A1 | * | 3/2003 | Roszell et al. ............. 424/70.13 |
| 2004/0126339 | A1 | * | 7/2004 | Roszell ........................... 424/59 |
| 2005/0255067 | A1 | * | 11/2005 | Leighton et al. ............. 424/70.2 |

FOREIGN PATENT DOCUMENTS

| | | | |
|---|---|---|---|
| GB | 2324036 A | * | 10/1998 |
| WO | WO 2007080411 A1 | * | 7/2007 |

OTHER PUBLICATIONS

Ratnayake, Wajira S., and David S. Jackson. "A new insight into the gelatinization process of native starches." Carbohydrate Polymers 67.4 (2007): 511-529.*

* cited by examiner

*Primary Examiner* — Kevin S. Orwig
*Assistant Examiner* — Peter Anthopolos
(74) *Attorney, Agent, or Firm* — Troutman Sanders LLP; Ryan A. Schneider; Troy S. Kleckley

(57) ABSTRACT

A depilatory composition which is an emulsion of hydrophobic particles in a continuous aqueous phase wherein the aqueous phase—includes at least one depilatory agent and the hydrophobic particles includes a vinyl polymer derivative and a polysaccharide.

11 Claims, 1 Drawing Sheet

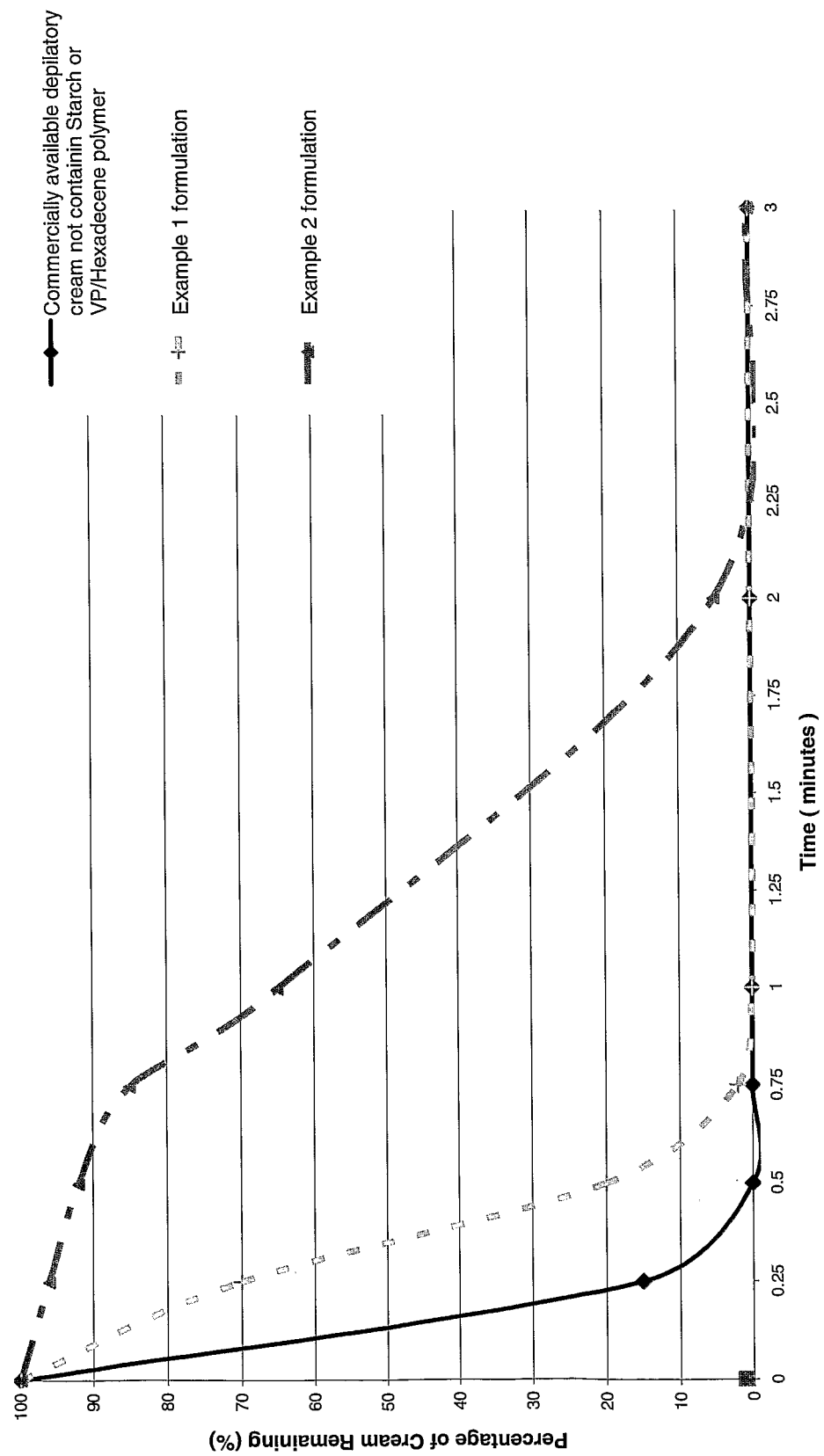

DEPILATORY COMPOSITION COMPRISING HYDROPHOBIC PARTICLES, PROCESS FOR PREPARATION AND METHOD OF USE

BENEFIT CLAIMS

This application is a US National Stage of International Application No. PCT/GB2008/004288, filed 24 Dec. 2008, which claims the benefit of GB 0800570.4, filed 14 Jan. 2008.

The present invention relates to depilatory compositions, their preparation, and methods for their use in removing hair from the skin of humans.

Compositions for removing superfluous body hair are known and are of various types. One type of composition requires initial heating before being applied to the skin in a generally molten state. It is then allowed to solidify before being removed from the skin together with unwanted hair. This is known in the art as epilation, as the hairs are uprooted from the skin.

Another type of composition is in the form of a cream, which can be applied to the skin at room temperature. The cream includes a substance that degrades hair keratin. Conventionally, the compositions are applied to the skin where unwanted hair is present, then left in place for a predetermined time to allow the keratin in the hair to become degraded. The composition along with degraded hair is then removed from the skin, usually with a tool such as a sponge or wipe or spatula. Such compositions are known in the art as depilatory compositions.

If the depilatory composition is left in contact with the skin for excessive lengths of time, there is a risk that the composition may cause irritation of the skin in some users. If it is present for too short a time, degradation of keratin may be inadequate, leading to only partial removal of the unwanted hair. In this specification, the period the composition must be left in contact with the hairy skin to achieve adequate hair degradation is referred to as the degradation period. Typical degradation periods are in the range 3 to 15 minutes.

In the art, the trend has been to make depilatory compositions sufficiently viscous so that they will stay in place on desired region of skin where superfluous hair removal is desired, without slipping to other regions of skin or falling off during the degradation period. In parallel, there has also been a trend to make the compositions easier to rinse from the skin, so that once the degradation period is over, the composition and degraded hairs can be rinsed easily from the skin. See for example EP0855900.

WO 99/02125 discloses depilatory compositions in the form of oil-in-water emulsions. The preferred depilatory compound is cited as potassium thioglycolate. A pH regulator is present, the preferred pH regulator being lime (calcium hydroxide).

A problem with prior art depilatory compositions arises from their ease of rinsing. The user generally applies the compositions in the bathroom by a bathtub, sink or shower, or even in a bath or shower, and must wait for several minutes before removing the composition, but is prevented from simultaneously carrying out any other procedures which could lead to the composition being inadvertently rinsed away or partially rinsed away. This would potentially lead to patches of hair remaining on the skin. So, for instance, with prior art compositions, the user would be inhibited from applying the composition to their legs then washing their upper body, or shampooing their hair, or shaving their armpits during the degradation period. This can lead to a considerable lengthening of the total time required for ablutions when removal of superfluous hair is desired.

It has now been found that these problems can be alleviated by providing a depilatory composition which remains in place on the skin for enough time for hair degradation to take place even when rinsed or immersed in water for short periods of time.

Therefore, according to a first aspect of the present invention, there is provided a depilatory composition which is an emulsion of hydrophobic particles in a continuous aqueous phase wherein the aqueous phase includes at least one depilatory agent and the hydrophobic particles includes a vinyl polymer derivative and a polysaccharide.

Surprisingly, the presence of a vinyl polymer derivative together with the polysaccharide in the composition leads to a considerable improvement in the adherence of the composition to the skin even when subjected to a stream of rinsing water.

In a second aspect, the invention provides a method of hair removal from human skin which includes the steps of
i) applying a composition according to the first aspect of the invention to the skin where superfluous hair is present,
ii) allowing the composition to remain in contact with the skin for a predetermined time, and
iii) removing the composition and degraded hair from the skin.

Preferably, a removal tool is used to remove the composition and degraded hair.

Further aspects of the invention are concerned with processes for preparing the depilatory compositions and their use for degrading hair keratin in a wet environment, where there is risk of accidental rinsing away of the composition, such as a bathroom.

It is particularly preferred that the modified PVP's are modified with a hydrophobic entity to make them oil phase soluble. It is particularly preferred that the polyvinyl polymer derivative is selected from PVP/hexadecane copolymer, PVP/eicosene copolymer and tricontanyl PVP.

Compositions of the present invention typically comprise from 0.1% to 5.0% by weight of the PVP derivative, preferably 0.5% to 3.5% by weight. However, it is particularly preferred that the PVP derivative is in the range 1.5% to 2.5% by weight, such as 2.0% by weight.

The polyvinyl polymer derivative typically has the formula A below:

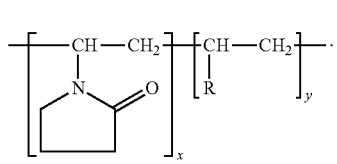

Formula A

A particularly preferred hexadecene copolymer is a VP/hexadecene copolymer preferably having a molecular weight from about 4000 to 13,000, such as 5000 to 11,000, mass units. A particularly preferred molecular weight is in the range 6,500 to 8,500, such as about 7,300. Such a copolymer provides the advantage of ease of incorporation of the hexadecene into the hydrophobic particles of the invention by melting and blending. A VP hexadecene suitable for use in compositions of the invention is a polymer with the structure $(C_{22}H_{41}NO)_x$.

It is particularly preferred that the polysaccharide is a starch, and/or is gelatinised.

The polysaccharide is typically present in an amount in the range 0.1 to 4.0% by weight of the composition. Preferably, the polysaccharide is present in an amount of no more than 3.0% by weight; further preferably less than 2.0% by weight. A particularly preferred range is 0.1 to 0.75% by weight of the composition.

According to a particularly preferred embodiment of the present invention, the polysaccharide is gelatinised. The polysaccharide is gelatinised prior to inclusion in the composition. The gelatinised polysaccharide gives rise to a smooth homogenous paste which is visibly more viscous.

It is particularly preferred that the polysaccharide is a starch. The starch may be maize/corn starch, potato starch, tapioca starch, wheat starch or rice starch It is particularly preferred that the polysaccharide is gelatinised starch, such as gelatinised corn starch (Zea Mays Starch).

According to a particularly preferred embodiment of the present invention, there is provided a depilatory composition which is an emulsion of hydrophobic particles in a continuous aqueous phase, wherein the aqueous phase includes at least one depilatory agent, and the hydrophobic particles includes starch (such as gelatinised starch) and PVP/hexadecane copolymer, PVP/eicosene copolymer and tricontanyl PVP. The starch and the PVP/hexadecane copolymer, PVP/eicosene copolymer and tricontanyl PVP are substantially as described hereinbefore.

The depilatory agent is a substance capable of degrading keratin. The depilatory agent, according to the present invention, may include a mixture of one or more depilatory agents. Preferred depilatory agents are sulfhydryl compounds, meaning a compound having an —S—H group. Suitable sulfhydryl depilatory agents include but are not limited to the group consisting of thioglycolic acid, cysteine, homocysteine, glutathione, thioglycerol, thiomalic acid, 2-mercaptopropionic acid, 3-mercaptopropionic acid, thiodiglycol, 2-mercaptoethanol, dithiothreitol, thioxanthene, thiosalicylic acid, thiolactic acid, thiopropionic acid, thiodiglycolic acid, N-acetyl-L-cysteine, lipoic acid, and cosmetically- and/or pharmaceutically acceptable salts of any of the foregoing compounds.

Preferred sulfhydryl compounds include thioglycolic acid, cysteine, glutathione, N-acetyl-L-cysteine, lipoic acid, thiosalicylic acid, and thiolactic acid and cosmetically- and/or pharmaceutically-acceptable salts thereof. More preferred sulfhydryl compounds include thioglycolic acid, cysteine, glutathione and N-acetyl-L-cysteine and cosmetically- and/or pharmaceutically acceptable salts thereof. The most preferred sulfhydryl compound is thioglycolic acid and cosmetically- and/or pharmaceutically-acceptable salts thereof. As used herein, "cosmetically- and/or pharmaceutically-acceptable salts" of the sulfhydryl compounds include, but are not limited to alkali metal salts, e.g., sodium, lithium, rubidium and potassium salts; alkaline earth metal salts, e.g., magnesium, calcium and strontium salts; non-toxic heavy metal salts, e.g., aluminium salts and zinc salts; boron salts; silicon salts; ammonium salts; trialkylammonium salts, e.g., trimethylammonium and triethylammonium; and tetralkylonium salts.

Preferred cosmetically- and/or pharmaceutically-acceptable salts of the sulfhydryl compound include sodium, potassium and calcium salts. Most preferred salts of the sulfhydryl compound are potassium and calcium salts.

Suitably, the composition comprises from 1 to 8% by weight, preferably from 2 to 6% by weight, of depilatory agent expressed as the acid form of the depilatory agent. For example, it is preferred that the composition comprises potassium glycolate at pH12.3, this is not expressed as potassium thioglycolate, but as the equivalent weight of thioglycolic acid.

Optionally, the composition includes an accelerator that will accelerate the keratin degradation reaction. Suitable accelerators include urea, thiourea, dimethyl isosorbide, ethoxydiglycol and methyl propyl diol. Preferably the accelerator is urea or methyl propyl diol. The composition according to the invention preferably comprises from 5% to 15% by weight, more preferably 7% to 10% by weight of an accelerator.

It is particularly preferred for the composition to comprise a pH regulator to assist in activating the depilatory agent, particularly when the depilatory agent is a sulfhydryl compound. Preferably the quantity and type of pH regulator is chosen to maintain the pH of the composition at a value greater than 5, preferably greater than 7, more preferably from 8 to 13, most preferably from 10 to 12.9, especially from 12 to 12.7. For example, by ensuring that the pH is about 12.1 to 12.7, depilation can occur within about 5 minutes, as desired by the user, without causing undue irritation. Higher pH levels can lead to irritation problems with some users.

The pH regulator preferably is in the continuous aqueous phase (between the hydrophobic particles) when present. Examples of the pH regulator include arginine (especially L-arginine), silicates (e.g. sodium or potassium silicate), calcium hydroxide and polyethyleneimine. Mixtures of pH regulators may be used. It is particularly preferred for the pH regulator also to include calcium hydroxide in an amount from 2 to 4% by weight of the composition. The pH regulator may be dissolved in the aqueous phase of the composition or may be present as solid particles dispersed throughout the composition.

Compositions according to the invention comprise hydrophobic particles distributed as an emulsion (an oil-in-water emulsion) in an aqueous continuous phase which is a liquid at 25° C. By aqueous it is meant that the continuous phase comprises at least 50% by weight of water, preferably 70% by weight or more based on the total weight of the continuous phase. The amount of water in the composition as a whole will typically be from 40% to 95% by weight of the composition.

The hydrophobic particles of the compositions of the invention may comprise non-polar oily or waxy materials which are insoluble in water (by insoluble is meant a solubility in water of 0.1% by weight or less at 25° C.) but must comprise a fatty alcohol. Preferably, the alkyl/alkenyl chain of the fatty material is fully saturated. Suitable fatty alcohols comprise from 8 to 22 carbon atoms, more preferably 16 to 22. A mixture of fatty alcohols may also be used. Preferred fatty alcohols include cetyl alcohol, stearyl alcohol and mixtures thereof.

Suitably, the amount of fatty alcohol in compositions of the invention is 3% or more, preferably 5% or more, most preferably 7% or more by weight of the composition.

Suitably, compositions of the invention comprise less than 20%, preferably less than 15%, more preferably less than 11% by weight of fatty alcohol.

Suitable waxes include beeswax, carnauba, baysberry, candelilla, montan, ozokerite, ceresin, hydrogenated castor oil (castor wax), synthetic waxes such as Fisher-Tropsch waxes, microcrystalline waxes, and mixtures thereof. Waxes such as triglycerides or glycol diesters of $C_{18}$ to $C_{36}$ fatty acids are also suitable as gelling agent for the oil phase.

Particles means finely divided parts, and encompasses solid particles, liquid particles and plastic or waxy particles. Preferably, the particles are solid at a temperature of 25° C. or less. Preferably, the particles are liquid at a temperature of 80°

C. or more in order to facilitate the preparation of the composition. The hydrophobic particles suitably have a mean diameter $D_{4,3}$ as measured by laser light scattering (using apparatus such as a Malvern Mastersizer™) from 0.1 to 50 micrometers, preferably from 0.5 to 20 micrometers, more preferably from 1 to 10 micrometers.

Preferably, compositions of the invention include an emulsifier to facilitate the emulsification of the hydrophobic particles in the continuous aqueous phase and to stabilise the emulsion against coalescence of the hydrophobic particles. In general the emulsifier is an anionic, cationic, non-ionic or zwitterionic surfactant. Preferably the emulsifier is a non-ionic surfactant.

Suitable nonionic surfactants include alkyl ethers of polyethylene glycol and/or polypropylene glycol, including mixed ethers and mixtures thereof. The emulsifier is suitably present in an amount of from 2% to 10%, most preferably from 3% to 8% by weight of the composition.

The compositions of the invention, in addition to the hydrophobic particles and the aqueous continuous liquid phase, may also include other ingredients that are conventionally present in depilatory formulations, such as perfumes, oils, and pigments (such as titanium dioxide) and thickeners such as a clay.

Suitable clays for thickening may include organophilic and layered clay minerals belonging to the geological classes of the smectites, the kaolins, the illites, the chlorites, the attapulgites and the mixed layer clays. Typical examples of specific clays belonging to these classes are: 1) smectites, e.g. montmorillonite, bentonite, pyrophyllite, hectorite, saponite, sauconite, nontronite, talc, beidellite; 2) illites, e.g., bravaisite, muscovite, paragonite, phlogopite; 3) chlorites, e.g., corrensite, penninite, donbassite, sudoite; 4) attapulgites, e.g., sepiolite, and polygorskyte.

The layered clay minerals may be either naturally occurring or synthetic. Preferred clay minerals for use in the present invention are natural or synthetic smectites and attapulgites, (particularly the hectorites, montmorillonites and bentonites,) and of these the hectorites are especially preferred. Many of the above clays are available commercially, and typical examples of commercial hectorites are the Laponites ex Laporte Industries Ltd., England; Veegum Pro and Veegum F ex R. T. Vanderbilt, USA; and the Barasyms, Macaloids and Propaloids ex Baroid Division, National Lead Company, USA. If a clay is used for thickening, it is preferably in an amount of from 0.1 to 10% by weight, more preferably from 0.1 to 1% by weight of the composition.

The inclusion of a clay, preferably sodium lithium magnesium silicate, is particularly advantageous, since this provides lithium, sodium and magnesium ions for the buffer system and improves the efficiency of depilation. It is particularly preferred if the clay is a synthetic hectorite clay such as Laponite™.

Other optional water-soluble thickening agents which may be used include Carbomer™ (Acrylic acid polymer, preferably cross-linked), acrylic polymer emulsions (e.g. acrylate/stereath-20 methracylate copolymer), cellulose based thickeners or natural thickeners such as gum arabic, alginates, carrageenan, locust bean gum, xanthan gum and polyvinyl alcohol. Mixtures of thickeners may be used.

A preferred method for preparing compositions according to the first aspect of the present invention includes the following steps:

1. The polysaccharide (such as maize/corn starch) is mixed into cold water and then heated to 75 deg C., the resultant premix is held for approximately one hour to gelatinise the polysaccharide;
2. In a separate vessel cetearyl alcohol, ceteareth 20, PPG-15 stearyl ether, mineral oil and modified PVP polymer are heated to form a melt which is the oil phase;
3. The oil phase is subsequently emulsified with the gelatinised polysaccharide (gelatinised starch) and cooled to 40 deg C.; and
4. The remaining ingredients including the thioglycolate premix are combined with the resultant mixture from 3 to form a depilatory cream.

According to a particularly preferred embodiment of the present invention, the polysaccharide, such as a starch, is gelatinised prior to mixing with other components of the composition.

It is envisaged that if the polysaccharide (starch) has already been pregelatinised (for example a pregelatinised grade), it can be added at the end with the other ingredients.

The depilatory agent and any optional accelerator is preferably not added until after the emulsion has been cooled to prevent degradation of the depilatory agent (which may occur at substantially elevated temperatures). Any optional ingredients may be added thereafter; however it is preferred for any clay to be added at an elevated temperature.

According to a further aspect of the present invention there is provided a method of hair removal from human skin including the steps of i) applying a composition according to the first aspect of the invention to the skin where superfluous hair is present, ii) allowing the composition to remain in contact with the skin for a predetermined time, iii) removing the composition and degraded hair using a removal tool, and iv) preferably washing the skin.

For this second aspect of the invention, it is preferred if the composition is applied to the skin with an application tool, giving the advantage that the composition does not come into contact with the users hands. In addition, the composition and degraded hair are preferably removed from the skin using a removal tool.

According to the invention there is further provided the use of a composition according to the invention to degrade hair keratin.

Throughout this specification, percentages of ingredients by weight are referenced to the weight of the total composition, unless otherwise specified. The following Examples illustrate the invention.

EXAMPLES

| Sample 1: % w/w | Sample 2: % w/w | Sample 3: % w/w | Sample 4 % w/w | INCI name |
|---|---|---|---|---|
| 7.8 | 7.8 | 7.8 | 7.8 | Cetearyl Alcohol |
| 3.1 | 3.1 | 3.1 | 3.1 | Ceteareth-20 |
| 1.05 | 1.05 | 1.05 | 1.05 | Paraffinum liquidum |
| 1.05 | 1.05 | 1.05 | 1.05 | PPG-15 Stearyl Ether (and) BHT |
| 2 | 2 | 0 | 0 | VP/Hexadecene copolymer |
| 0 | 0 | 2 | 0 | PVP/Eicosene Copolymer |
| 0 | 0 | 0 | 2 | Tricontanyl PVP |
| 0.6 | 0.6 | 0.6 | 0.6 | Propylene Glycol, CI 7789, CI 45380:3 |
| 3.75 | 3.75 | 3.75 | 3.75 | Calcium Hydroxide |
| 0.1 | 0.1 | 0.1 | 0.1 | Sodium Gluconate |
| 0.5 | 0.5 | 0.5 | 0.5 | Magnesium Trisilicate |
| 8 | 8 | 8 | 8 | Urea |
| 0.2 | 0.2 | 0.2 | 0.2 | Lithium Magnesium Sodium Silicate |
| 0.56 | 0.56 | 0.56 | 0.56 | Parfum, Linalool, Butylphenyl |

-continued

| Sample 1: % w/w | Sample 2: % w/w | Sample 3: % w/w | Sample 4 % w/w | INCI name |
|---|---|---|---|---|
| | | | | Methylpropional |
| 0.025 | 0.025 | 0.025 | 0.025 | Hydrated silica |
| 0.1 | 0.1 | 0.1 | 0.1 | Aqua, Propylene glycol Dicaprylate/dicaprate, *Nelumbo nucifera* flower extract, xanthan gum, phenoxyethanol, methylparaben, ethylparaben, butylparaben, propylparaben, Isobutylparaben |
| 0.25 | 0 | 0.25 | 0.25 | *Zea Mays* Starch |
| 0.275 | 0.275 | 0.275 | 0.275 | Potassium hydroxide |
| 12.9 | 12.9 | 12.9 | 12.9 | Aqua, Potassium hydroxide, Thioglycolic acid |
| 57.7 | 57.975 | 57.775 | 57.775 | Aqua |
| 100.0 | 100.0 | 100.0 | 100.0 | |

The compositions identified in table 1 were prepared by emulsifying a melt at 70° C. formed from the cetearyl alcohol, ceteareth 20, ppg-15 stearyl ether paraffin wax and VP hexadecene copolymer, PVP/Eicosene Copolymer or the Tricontanyl PVP.

The melt was then mixed with the gelatinised starch (Examples 1, 3 and 4). This mix was subsequently cooled to 40° C. prior to addition of the depilatory agent: other ingredients were blended while cooling from 70 to 40° C.

The water resistance of a depilatory cream having the composition given in Example 1 (with gelatinised starch) and Example 2 (without gelatinised starch) were tested in vitro, as follows:
1. The compositions manufactured in Examples 1 and 2 were applied to a dry bathroom tile using a metal template. The template (6 cm×12 cm) allows the cream to be spread to a depth of 1 mm
2. Whilst the template is still in place, the surface of the cream is smoothed over to ensure there are no flaws.
3. A shower head is place 10 cm above the cream patch. Water at 40 deg C. and flowing at 174-190 mL/s is allowed to run over the cream. At one minute intervals, the % cream left is estimated.

The results can be seen in FIG. 1

The resultant composition demonstrated improved reduced rinsability when compared to prior art depilatory compositions.

The invention claimed is:

1. A depilatory composition which is a cream emulsion of hydrophobic particles in a continuous aqueous phase wherein the aqueous phase includes at least one depilatory agent and the hydrophobic particles includes a vinyl polymer derivative and a polysaccharide, wherein the vinyl polymer derivative is a polyvinyl polymer derivative;
   wherein the polyvinyl polymer derivative is selected from the group consisting of PVP/hexadecane copolymer, PVP/eicosene copolymer and tricontanyl PVP; and
   wherein the polysaccharide is pre-gelatinized.

2. A composition according to claim 1, wherein the polyvinyl polymer derivative is modified with a hydrophobic entity to make it oil phase soluble.

3. A composition according to claim 2, which includes from 0.1% to 5.0% by weight of the PVP derivative.

4. A composition according to claim 3, wherein the PVP derivative is present in an amount in the range 1.5% to 2.5% by weight.

5. A composition according to claim 1, wherein the polysaccharide is a starch.

6. A composition according to claim 1, wherein the polysaccharide is present in an amount in the range 0.1% to 4.0% by weight of the composition.

7. A composition according to claim 1, wherein the polysaccharide is present in an amount of no more than 3.0% by weight.

8. A composition according to claim 5, wherein the starch is selected from the group consisting of maize/corn starch, potato starch, tapioca starch, wheat starch and rice starch.

9. A method of hair removal from human skin comprising:
   applying a composition according to claim 1 to the skin where superfluous hair is present, allowing the composition to remain in contact with the skin for a predetermined time, and removing the composition and degraded hair from the skin.

10. A composition according to claim 2, which includes from 0.5% to 3.5% by weight of the PVP derivative.

11. A composition according to claim 1, wherein the polysaccharide is present in an amount of no more than 2.0% by weight.

* * * * *